US00PP15629P2

(12) United States Plant Patent
Bernuetz

(10) Patent No.: US PP15,629 P2
(45) Date of Patent: Mar. 8, 2005

(54) ***BRACTEANTHA* PLANT NAMED 'OHB003790'**

(50) Latin Name: *Bracteantha bracteata*
Varietal Denomination: OHB003790

(75) Inventor: Andrew Bernuetz, Silverdale (AU)

(73) Assignee: Oasis Horticulture Pty. Ltd, Winmalee (AU)

( * ) Notice: Subject to any disclaimer, the term of this patent is extended or adjusted under 35 U.S.C. 154(b) by 0 days.

(21) Appl. No.: 10/741,486

(22) Filed: Dec. 19, 2003

(51) Int. Cl.[7] ..... A01H 5/00
(52) U.S. Cl. ..... Plt./359
(58) Field of Search ..... Plt./359

*Primary Examiner*—Anne Marie Grunberg
(74) *Attorney, Agent, or Firm*—Wood, Phillips, Katz, Clark & Mortimer

(57) ABSTRACT

A new and distinct *Bracteantha* plant named 'OHB003790', characterized by its large inflorescences of yellow-colored involucral bracts and orange colored disc florets, dark green-colored foliage, and compact upright growth habit.

1 Drawing Sheet

Latin name of the genus and species of plant claimed: *Bracteantha bracteata.*
Variety denomination: 'OHB003790'

BACKGROUND OF THE INVENTION

The present invention comprises a new and distinct *Bracteantha* plant botanically known as *Bracteantha bracteata* and hereinafter referred to by the cultivar name 'OHB003790'.

The new cultivar was developed by the inventor in a controlled breeding program during November 2000, a Winmalee NSW, Australia. The objective of the breeding program was the development of *Bracteantha* cultivars with a compact growth habit, numerous involucral bracts having attractive colors, dark green-colored foliage and large inflorescences that remain open under low light conditions.

The female (seed) parent of 'OHB003790' was the cultivar 'Argyle Star' (not patented) characterized by its white-colored, single flowers, and medium growth habit. The male (pollen) parent of 'OHB003790' was a mix of pollen from 'Antique Shades' (U.S. Plant Pat. No. 13,559), 'Copper' (U.S. Plant Pat. No. 13,905) and 'Cream' (U.S. Plant Pat. No. 14,915). 'OHB003790' was selected as a single flowering plant within progeny of the above stated cross-pollination in April 2001 at Winmalee, NSW, Australia.

Asexual reproduction of the new cultivar by terminal stem cuttings since April 2001 at Winmalee, NSW, Australia and West Chicago, Ill. has demonstrated that the new cultivar reproduce true to type with all the characteristics, as herein described, firmly fixed and retained through successive generations of such asexual propagation.

SUMMARY OF THE INVENTION

The new cultivar has not been observed under all possible environmental conditions to date. Accordingly, it is possible that the phenotype may vary somewhat with variations in the environment, such as temperature, light intensity, and day length without, however, any variance in genotype.

It was repeatedly found that the cultivar of the present invention:

1. Exhibits large inflorescences of yellow-colored involucral bracts and orange colored disc florets, 2. Forms dark green-colored foliage;
3. Exhibits a good basal branching character, and
4. Exhibits a compact upright growth habit.

Plants of the new cultivar differ from plants of the female parent primarily in flower color, flower form and growth habit, and from plants of the male parent primarily in flower color.

Of the many *Bracteantha* cultivars known to the inventor, the most similar to 'OHB003790' is 'Redbragol' (U.S. Plant Pat. No. 12,988). However, in a side-by-side comparison at West Chicago, Ill., plants of 'OHB003790' differed from plants of 'Redbragol' in the following characteristics:

1. Plants of the new cultivar have slightly larger inflorescences than plants of 'Redbragol',
2. Plants of the new cultivar have smaller leaves than plants of 'Redbragol', and
3. Plants of the new cultivar have lighter yellow-colored involucral bracts than plants of 'Redbragol'.

BRIEF DESCRIPTION OF THE PHOTOGRAPHS

The accompanying photographs shows as nearly true as it is reasonably possible to make the same in color illustrations of this type, typical flower and foliage characteristics of the new cultivar. Colors in the photographs differ slightly from the color values cited in the detailed description, which accurately describe the colors of 'OHB003790'. The plants were grown for 13 weeks in a greenhouse at West Chicago, Ill.

FIG. 1 illustrates a side view of the overall growth and flowering habit of 'OHB003790'.

FIG. 2 illustrates a close-up view of a single fully open inflorescence of 'OHB003790'.

DETAILED BOTANICAL DESCRIPTION

The chart used in the identification of colors described herein is the R.H.S. Colour Chart of The Royal Horticultural Society, London, England, 1995 edition, except where general color terms of ordinary significance are used. The color values were determined on Aug. 13, 2003. The readings were taken between 10:00 and 11:00 a.m. under natural daylight conditions. The plants were produced from terminal stem cuttings taken from stock plants and grown in a polycarbonate-covered greenhouse under conditions comparable to those used in commercial practice. The plants were grown in 10 cm pots utilizing a soilless growth medium. Greenhouse temperatures were maintained at approximately 65°–75° F. during the day and approximately 55°–60° F. during the night. Greenhouse light levels were maintained at approximately 5,000–8,000 footcandles during the day. Plants used for the following descriptions and measurements were grown for 13 weeks from the planting of rooted cuttings.

Botanical classification: *Bracteantha bracteata* cultivar 'OHBO03790'.

Parentage:

*Female parent.*—Argyle Star (not patented).

*Male parent.*—Mixtures of pollen from the *Bracteantha* varieties, 'Antique Shades', 'Copper' and 'Cream'.

Propagation:

*Type cutting.*—Terminal stem.

*Time to initiate roots.*—Approximately 6 to 9 days.

*Time to form roots.*—Approximately 3 weeks.

*Crop time.*—Approximately 6–8 weeks from the planting of rooted cuttings.

Plant description:

*Habit of growth.*—Moderate. A mature plant, 13 weeks after the planting of a rooted cutting, commonly measures approximately 23.1 cm in height and approximately 29.8 cm in diameter (area of spread).

*Form.*—Upright, mounded.

*Branching habit.*—Freely basal branching. Commonly develops approximately 7 branches.

*Branch.*—Length: Approximately 7.4 cm. Diameter: Approximately 5 mm. Texture: Densely pubescent. Color: 144A. Internode length: Approximately 1 cm.

*Foliage.*—Type: Simple. Arrangement: Alternate. Shape: Lanceolate. Margin: Entire. Apex: Broadly acute. Base: Clasping. Quantity per lateral branch: Approximately 13. Size: Length: Approximately 7.9 cm. Width at widest point: Approximately 1.1 cm. Texture of upper and lower surfaces: Rough. Color of upper surface: 139A. Color of lower surface: Darker than 138A. Venation pattern: Parallel. Color of venation of both surfaces: Closest to 145B.

Flowering description:

*Flowering habit.*—Free and continuous flowering, above foliage.

*Natural flowering season.*—Year-round in a greenhouse environment and from spring through autumn in an outdoor garden.

Inflorescence description:

*Type.*—Composite, persistent and not fragrant.

*Diameter.*—Approximately 5.4 cm.

*Depth.*—Approximately 2 cm.

*Quantity per branch.*—Approximately 2.

*Bud.*—Just before color: Depth: 1.5 cm. Diameter: 1.3 cm. At first color: Depth: 2 cm. Diameter: 4 cm. Color: 7B with overlay of 164A.

*Flower arrangement*—Acropetally on a capitulum.

*Peduncle.*—Length: Approximately 12.9 cm. Diameter: Approximately 2 mm. Strength: Strong. Aspect: Erect to slightly acute. Color: 144A. Texture: Lanate.

*Involucral bracts.*—Quantity: Approximately 176 arranged in several whorls. Aspect: Appear flat at maturity then become downwardly pointing with age. Appearance: Smooth, papery. Shape: Linear. Outermost bracts: Length: 1.6 cm. Width: 7 mm. Innermost bracts: Length: 1 cm. Width: 2 mm. Color: Upper and lower surface of fully opened bracts: Closest to 9A.

*Capitulum.*—Diameter: Approximately 2.2 cm. Depth: Approximately 7 mm.

*Disc floret.*—Quantity: Approximately 415. Shape: Tubular. Length: Approximately 5 mm. Width: Approximately 1 mm. Color: 24A. Reproductive organs: Stamen quantity: 5. Anther shape: Linear. Anther color: 15C. Pistil quantity: 1 per disc floret. Pistil length: Approximately 1.4 cm. Amount of pollen: Moderate. Pollen color: 7C. Stigma length: 2 mm. Stigma color: 17B. Style length: 7.5 mm. Style color: 4D.

*Lastingness of blooms.*—Flowers on the plant remain fresh for approximately 18 days. The flowers are not used as fresh cut flowers, however, they would be expected to last indefinitely as dried flowers but may fall apart after six to twelve months.

Seed and fruit development: Neither seed nor fruit development has been observed.

Disease and pest resistance: Resistance to pathogens and pests common to *Bracteantha* has not been observed.

What is claimed is:

1. A new and distinct cultivar of *Bracteantha* plant named 'OHB003790' substantially, as herein shown and described, which:

1. Exhibits large inflorescences of yellow-colored involucral bracts and orange colored disc florets,
2. Forms dark green-colored foliage,
3. Exhibits a good basal branching character, and
4. Exhibits a compact upright growth habit.

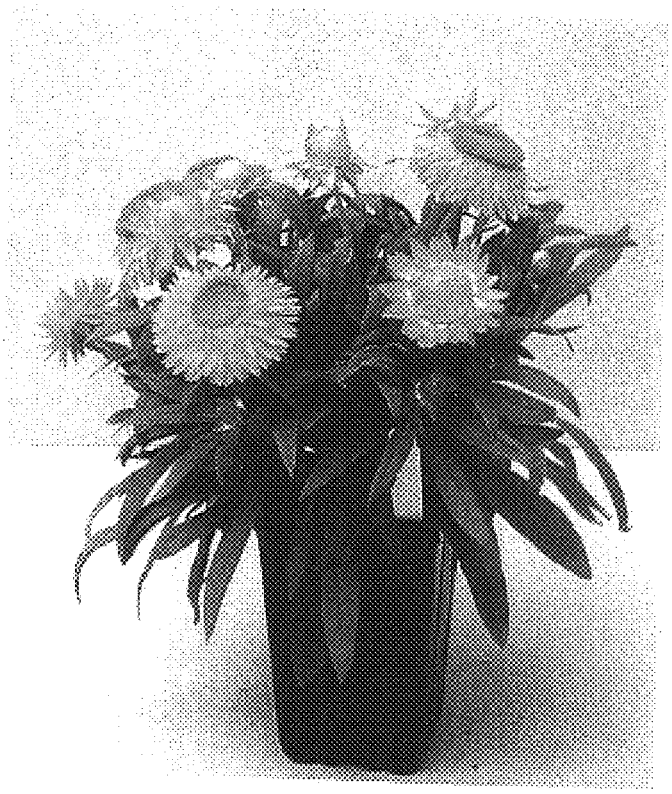
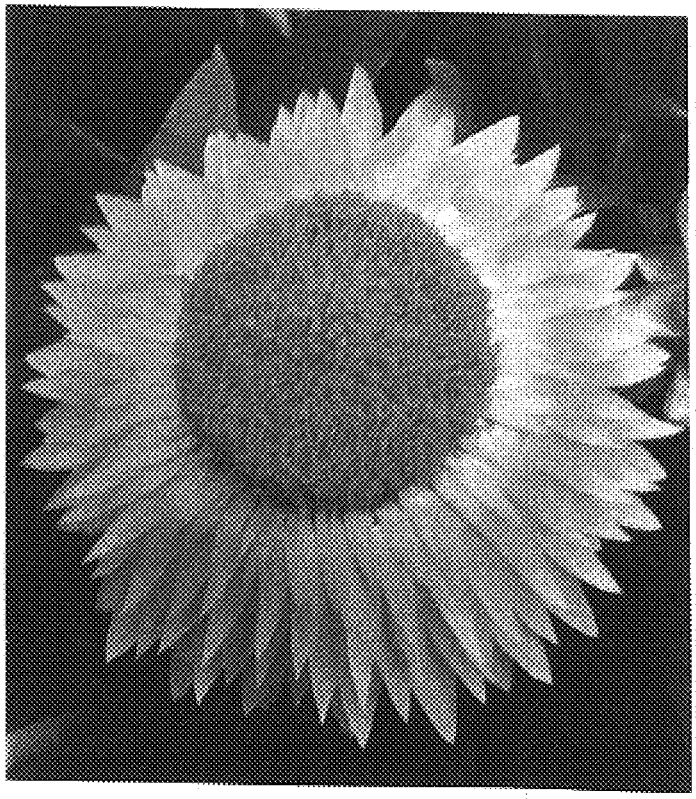

* * * * *